(12) United States Patent  
Accordino

(10) Patent No.: US 8,043,291 B2
(45) Date of Patent: Oct. 25, 2011

(54) BONE GRAFT HARVEST DEVICE

(76) Inventor: Joseph Accordino, Astoria, NY (US)

( * ) Notice: Subject to any disclaimer, the term of this patent is extended or adjusted under 35 U.S.C. 154(b) by 970 days.

(21) Appl. No.: 11/602,598

(22) Filed: Nov. 21, 2006

(65) Prior Publication Data

US 2007/0118050 A1 May 24, 2007

Related U.S. Application Data

(60) Provisional application No. 60/739,197, filed on Nov. 23, 2005.

(51) Int. Cl.
A61B 17/00 (2006.01)
(52) U.S. Cl. .......................................................... 606/79
(58) Field of Classification Search .................... 606/84, 606/79
See application file for complete search history.

(56) References Cited

U.S. PATENT DOCUMENTS

| | | | | |
|---|---|---|---|---|
| 1,493,240 A | * | 5/1924 | Bohn | 606/170 |
| 3,628,524 A | * | 12/1971 | Jamshidi | 600/567 |
| 4,002,092 A | * | 1/1977 | Smith et al. | 83/55 |
| 5,084,010 A | * | 1/1992 | Plaia et al. | 604/22 |
| 5,304,193 A | * | 4/1994 | Zhadanov | 606/182 |
| 5,435,672 A | * | 7/1995 | Hall et al. | 408/68 |
| 6,679,890 B2 | * | 1/2004 | Margulies et al. | 606/94 |
| 6,767,354 B2 | * | 7/2004 | Johanson et al. | 606/179 |
| 2006/0004369 A1 | * | 1/2006 | Patel et al. | 606/79 |

* cited by examiner

Primary Examiner — Thomas C. Barrett
Assistant Examiner — David Bates
(74) Attorney, Agent, or Firm — Gerald E. Hespos; Michael J. Porco

(57) ABSTRACT

A bone harvesting tool includes an elongate hollow collection cannula with a lumen for receiving harvested bone tissue. Holes are formed through the collection cannula to permit visual observation of the volume of bone tissue that has been collected. Cutting blades are mounted to the distal end of the collection cannula and are configured for cutting into bone tissue. The cutting blades are aligned so that the harvested bone tissue advances proximally into the lumen of the collection cannula. A guide pin is telescoped into the collection cannula and through the blades. The guide pin is employed for initial positioning of the tool on the bone. A plug near the distal end of the guide pin enables the guide pin to be used for expelling the collected bone tissue from the collection cannula.

6 Claims, 3 Drawing Sheets

BONE GRAFT HARVEST DEVICE

This application claims priority on U.S. Provisional Patent Appl. No. 60/739,197, filed Nov. 23, 2005.

BACKGROUND OF THE INVENTION

1. Field of the Invention

The invention relates to a bone harvesting device for collecting bone tissue that can be used in orthopedic procedures.

2. Description of the Related Art

Many orthopedic procedures require bone tissue to be harvested at one location on a patient for use at another location on the patient. For example, some patients experience a deterioration of the discs between vertebrae due to disease or injury. The deterioration of the discs causes the vertebrae to impinge upon nerves in and near the spine. The condition is extremely painful and debilitating. One procedure for addressing this problem is to fuse vertebrae together on opposite sides of the damaged disc. Spinal fusion surgery may include implantation of harvested bone tissue in the region between the vertebrae that are to be fused.

Bone tissue also may be harvested from one location to help heal a broken bone at a different location. For example, a severe fracture may completely sever a bone and may produce bone fragments in areas near the fracture. A severe break of this type often requires surgical intervention to remove some of the bone fragments. Additionally, a plate or rod may be implanted to provide structural support for the broken bone. Bone tissue harvested from one location may be implanted across the fracture and adjacent to the bone plate or rod. The harvested bone tissue will regenerate and contribute to structural support across the fracture.

Many patients experience disease or injury at joints. Diseased or damaged joints may require implantation of a prosthetic joint to supplement a portion of the diseased or damaged natural joint or to completely replace the natural joint. For example, total hip replacement requires the head of the natural femur to be removed and replaced by a prosthetic component. The prosthetic component includes a stem that must be inserted into a hole bored in the intramedullary cavity of the femur. Harvested bone tissue may be implanted around the stem of the femoral component of the prosthetic joint to enhance the support of the joint in the natural femur. Similarly, a socket may be implanted in a cavity prepared in the hip of the patient. Harvested bone tissue may be implanted around the prosthetic socket to provide the necessary support for the socket.

Many tools and techniques are employed for harvesting bone tissue. For example, some surgeons employ a reamer that is structurally and functionally similar to a cheese grater. The reamer may be generally cylindrical or spherical and may be formed from a thin stainless steel material. A plurality of openings are formed through the wall of the reamer and at least one side of each opening is sharpened and bulged to define a cutting edge that can cut into the bone tissue. The reamer is rubbed against or rotated against a targeted area for bone harvesting. As a result, bone tissue is cut from the bone and accumulates inside the reamer. The surgeon then must collect the accumulated bone tissue from the inside of the reamer in much the same way that grated cheese is accumulated from the inside of a cheese grater. Some reamers have worked well. However, it often is difficult to precisely target a location from which bone will be harvested with a reamer. Additionally, it is difficult for a surgeon to accurately determine how much bone tissue has been harvested. In some instances, too much bone tissue is accumulated in the reamer, thereby creating unnecessary trauma at the site of the bone harvesting. In other instances, too little bone tissue is harvested and the surgeon must revisit the site of the harvesting to collect additional tissue.

Some surgeons employ an auger-type tool to bore a hole in the bone at the site where the bone tissue is to be harvested. The auger is a rotating tool that produces bone debris in much the same way that a conventional drill produces sawdust when drilling into a piece of wood. This bone harvesting technique also requires the surgeon to guess about the volume of bone tissue that is being collected. Furthermore, the harvested bone tissue is not collected conveniently by the anger.

In view of the above, it is an object of the subject invention to provide a tool for harvesting bone tissue from specified locations and in clearly definable amounts.

It is another object of the subject invention to provide a bone harvesting tool that can be utilized easily by a surgeon.

SUMMARY OF THE INVENTION

A further object of the subject invention is to provide a bone harvesting tool capable of being reused.

The invention is directed to a bone harvesting tool that can be used for harvesting bone tissue in specified and controllable amounts for use at another location on a patient. The tool includes a collection cannula, a cutting device attached or attachable to one end of the collection cannula, drive means attached or attachable to the end of the collection cannula remote from the cutting device and a guide pin removably associated with the collection cannula.

The collection cannula preferably is an elongate hollow tube formed from a metallic material, such as stainless steel. The collection cannula has a proximal end that can be placed in communication with the driving means and a distal end that receives the cutting device. The collection cannula may include a plurality of openings at spaced apart locations between the proximal and distal ends, and preferably at a plurality of equally spaced locations extending from the distal end towards the proximal end. The openings are sufficiently large to enable a surgeon to observe bone tissue that has been harvested from the patient and collected in the cannula. The collection cannula also may include indicia along external surface. The indicia may correspond to distance dimensions from the distal end towards the proximal end so that the surgeon can accurately gauge the depth of insertion of the blade into the patient. Additionally, the surgeon can use the indicia on the external surface of the collection cannula to determine the precise amount of bone tissue that has been harvested and accumulated in the collection cannula.

The cutting device of the bone harvesting tool may include opposite proximal and distal ends. The proximal end of the cutting device may be an annular mounting ring configured for releasable engagement with the distal end of the collection cannula. In this regard, the distal end of the collection cannula may include an array of external threads, and the proximal end of the cutting device may include a corresponding array of internal threads. The cutting device may further include a plurality of blades extending from the mounting ring towards the distal end of the cutting device. The blades may include side cutting edges that are angularly aligned to the longitudinal axis of the collection cannula. The extreme distal ends of each blade also may be sufficiently sharp to cut into tissue, such as bone tissue.

The drive means of the bone harvesting tool may comprise at least one handle and/or at least one knob mounted to or near the proximal end of the collection cannula. In a preferred embodiment, a handle is mounted near the proximal end of the collection cannula and extends out transversely from the collection cannula. The knob may be mounted releasably to the extreme proximal end of the collection cannula. The knob may be generally semi-spherical and may include an array of knurling on the exterior to facilitate manual gripping by the surgeon.

The guide pin is an elongate metallic member dimensioned to pass through the hollow collection cannula and at least partly through the interior of the cutting device. The guide pin preferably has a proximal end and a sharply pointed distal end. Portions of the guide pin near the proximal end preferably include knurling to facilitate digital manipulation of the guide pin. Portions of the guide pin near the distal end preferably define a plug dimensioned to be received slidably within the collection cannula. As a result, distal portions of the guide pin can slide longitudinally within the collection cannula, but cannot move significantly in directions transverse to the longitudinal direction of the collection cannula. The guide pin preferably has a length that exceeds the length of the combined collection cannula, cutting device and knob. However, the proximal end of the guide pin will not project proximally beyond the proximal end of the collection cannula and knob when the sharply pointed distal end of the guide pin projects distally to the maximum extent beyond the end of the cutting device.

The bone harvesting tool of the subject invention is employed by releasably attaching the proximal end of the cutting device to the distal end of the collection cannula. The guide pin then is advanced axially through the collection cannula and partly through the cutting device. The knob then may be mounted over the proximal end of the positioning pin and may be threaded into engagement with the proximal end of the collection cannula.

The pointed distal end of the guide pin may be tapped into the bone at a specific targeted location from which bone is to be harvested. The elongate collection cannula and positioning pin enable the entire bone harvesting tool to be aligned at a preferred angle relative to the bone. The surgeon then rotates bone harvesting tool so that the blades of the cutting device advance into the targeted area of the bone for cutting away at the bone tissue. In a preferred embodiment, the surgeon applies axial pressure to the knurled knob at the proximal end of the collection cannula while utilizing the handle to rotate the entire tool about the longitudinal axis of the collection cannula. This axial force and rotational movement of the bone harvesting tool will cause the blades to cut into the bone of the patient. As a result, bone tissue will advance into the hollow interior defined by the cutting device and by the collection cannula. The surgeon can observe the depth of advance of the cutting device into the patient based on the indicia marked on the exterior of the collection cannula. Additionally, the surgeon can accurately determine the amount of bone tissue that has been harvested merely by observing the openings in the collection cannula. The collection of bone tissue in the cannula will cause the guide pin to advance proximally within the collection cannula. This proximal movement of the guide pin provides another indication of the volume of bone tissue that has been harvested.

The surgeon removes the bone harvesting tool from the harvesting site when the selected volume of bone tissue has been harvested and may remove the cutting device from the collection cannula. The collected bone tissue then can be transferred to another location on the patient or to an appropriate receptacle for subsequent use merely by urging the guide pin distally. As a result, the plug of the guide pin will force the harvested bone tissue distally through the collection cannula.

The bone harvesting tool may comprise a system of tools with parts that can be interchanged with one another. For example, cutting devices with blades of different dimensions or different angular orientations can be used in accordance with the bone harvesting needs of a patient. Additionally, the cross-sectional dimensions of the collection cannula can be varied in accordance with the size of the patient and the bone harvesting needs. Still further, the means for axially advancing and rotating the tool can be varied from the knob and handle of the preferred embodiment. In certain embodiments, a drill or other rotating tool can be employed. Additionally, these various components of different cross-sectional dimensions preferably are configured for interchangeable mating with one another.

DETAILED DESCRIPTION OF THE PREFERRED EMBODIMENT

Figure 1:
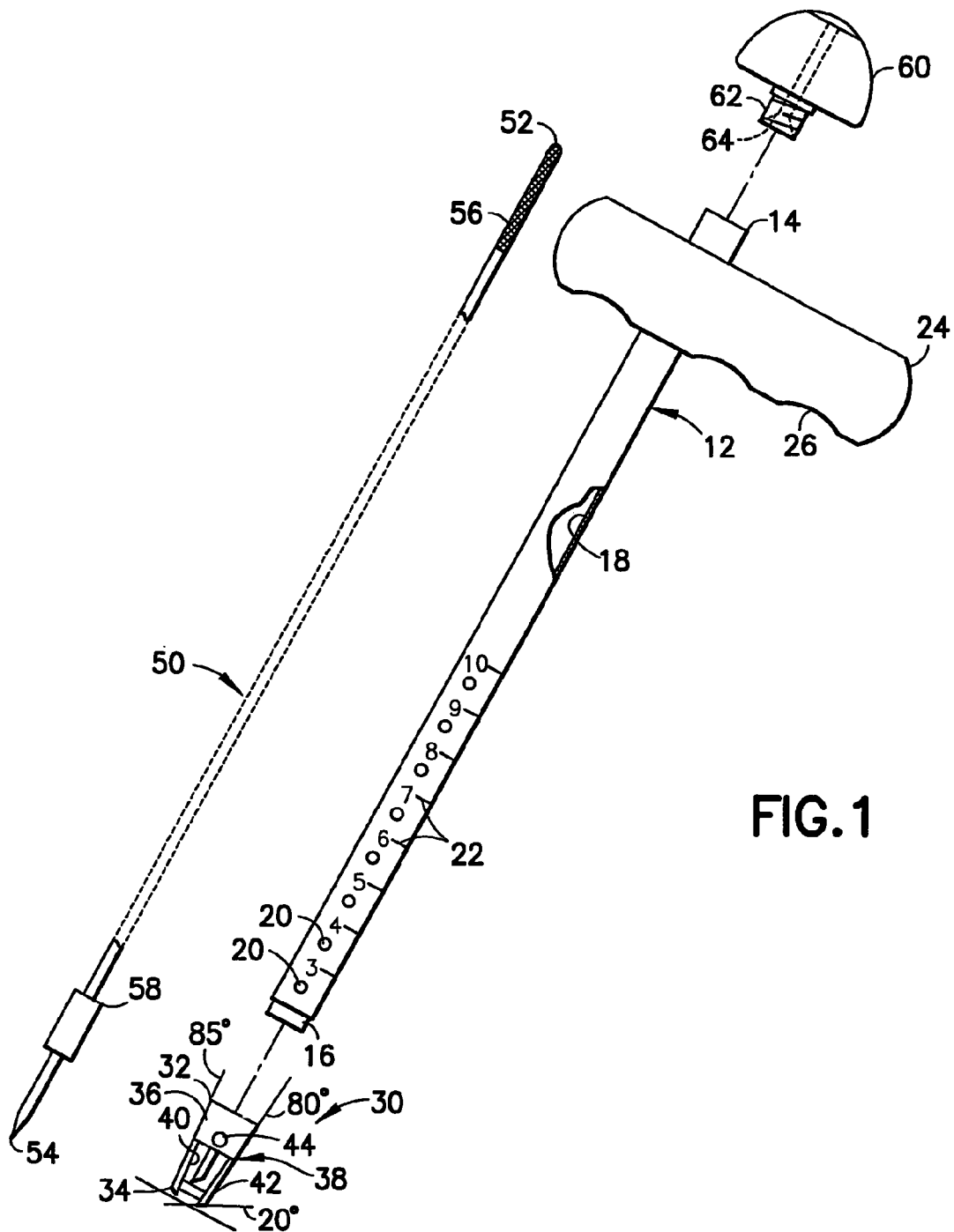
FIG. 1 is an exploded perspective view of a bone harvesting tool in accordance with the subject invention.
Figure 2:
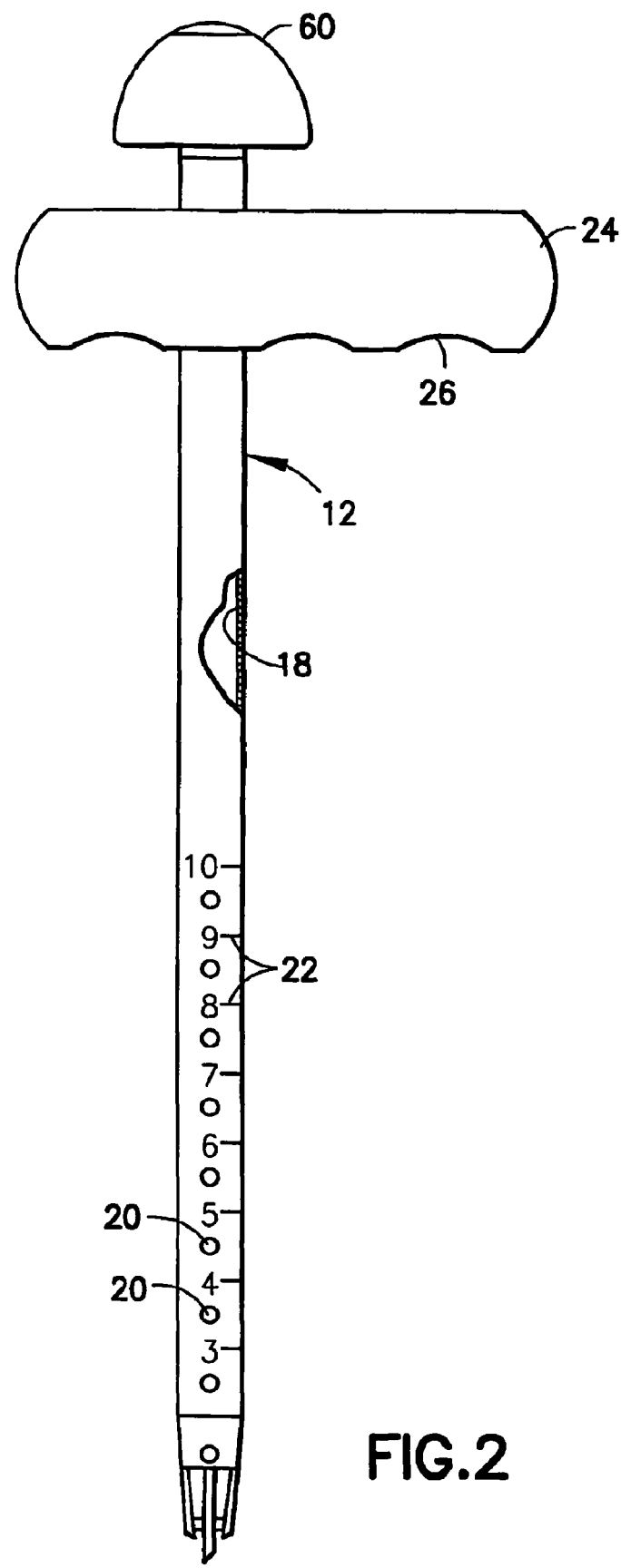
FIG. 2 is an assembled elevational view of the bone harvesting device in a ready-to-use condition.
Figure 3:
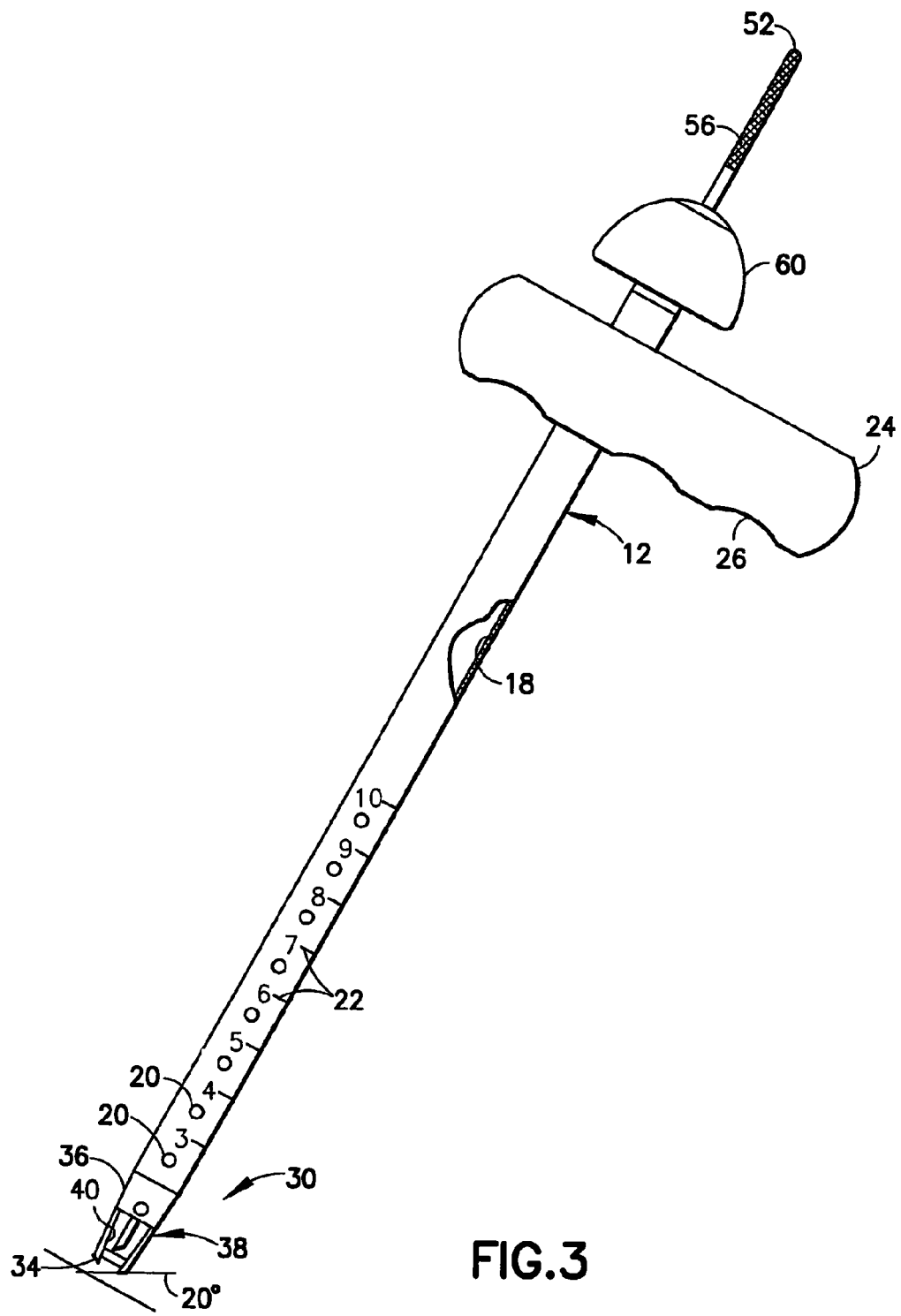
FIG. 3 is a side elevational view of the bone harvesting tool after collection of a selected volume of bone tissue.

A bone harvesting tool in accordance with the subject invention is identified generally by the numeral 10 in FIGS. 1-3. The bone harvesting tool includes an elongate substantially cylindrical collection cannula 12 having a proximal end 14, a distal end 16 and a lumen 18 extending between the ends. The proximal end 14 of the collection cannula 12 is formed with an array of internal threads. The distal end 16 of the collection cannula 12 is formed with an array of external threads. The collection cannula 12 includes a plurality of openings 20 formed therethrough at equally spaced intervals extending substantially from the distal end 16 towards the proximal end 14. The opening are sufficiently small to prevent excessive discharge of bone tissue from the lumen 18 through the openings 20. However, the openings 20 are sufficiently large to permit visual observation of bone tissue accumulated within the lumen 18. The collection cannula 12 further includes numeric indicia 22 at equally spaced locations along the outer surface of the collection cannula 12 from the distal end 16 towards the proximal end 14. The numeric indicia 22 preferably include sequential numbers so that a surgeon can gauge the depth of the collection cannula 18 into a patient and so that the surgeon can accurately gauge the amount of blood tissue that has been collected.

The collection cannula 12 preferably is formed from rigid substantially inert metallic material, such as stainless steel. The dimensions of the collection cannula are selected in accordance with the intended application. In a preferred embodiment, the collection cannula 12 defines a width of about 8-12 mm, and most preferably about 9.5 mm. The length of the collection cannula 12 preferably is in a range of 10-25 cm, and most preferably about 18 cm.

A handle 24 is mounted rigidly to the collection cannula at a location spaced slightly from the proximal end 14. The handle 24 preferably includes a plurality of finger grips 26 on the surface of the handle 24 facing towards the distal end 16.

The bone harvesting tool 10 further includes a cutting device 30 for mounting to the collection cannula 12. More particularly, the cutting device 30 includes opposite proximal and distal ends 32 and 34 respectively. A mounting ring 36 extends distally from the proximal end 32 and includes an array of internal threads configured for threaded engagement with the external threads at the distal end 16 of the collection cannula 12. The mounting ring 36 preferably includes an aperture 38 extending therethrough. The aperture 44 is configured to receive a pin (not shown) to facilitate threaded engagement of the cutting device 30 onto the distal end 16 of the collection cannula 12 without manually engaging sharp portions of the cutting device 30. Three blades 40 are spaced equally from one another about the periphery of the cutting device 30 and extend from the mounting ring 36 to the distal end 34 of the cutting device 30. Each blade 40 has a beveled side cutting edge 42 and an end cutting edge 44. The side cutting edges 42 preferably are aligned at approximately an 80° angle to the longitudinal axis of the collection cannula 12. The outer peripheral surface regions of the blades 40 are aligned slightly closer to being parallel to the longitudinal axis of the collection cannula 12, but still converge slightly towards the longitudinal axis at further distance in the distal direction. The end cutting edges 44 of each cutting blade 40 are aligned at an angle of about 20° to a plane extending normal to the longitudinal axis of the collection cannula 12. The sizes and angular alignments of the blades 40 can vary in accordance with the material from which the cutting device is formed and the relative dimensions of the material. These limitations can be selected by those skilled in this technology.

The bone harvesting tool 10 further includes guide pin 50 having a proximal end 52 and a sharply pointed distal end 54. The guide pin 50 defines a length that exceeds the combined length of the collection cannula 12 and the cutting device 30. Regions of the guide pin 50 adjacent the proximal end 52 preferably include a pattern of knurling 56 to facilitate digital manipulation of the guide pin 50. A plug 58 is formed on the guide pin 50 spaced slightly from the sharply pointed distal end 54. The plug 58 defines an outside diameter slightly smaller than the inside diameter defined by the lumen 18. Additionally, the outside diameter of the plug 58 is slightly larger than the inside diameter of the mounting ring 36 of the cutting device 30. Thus, the plug 58 prevents significant wobbling of the guide pin 50 in the collection cannula 12. Furthermore, the plug 58 limits the range of proximal-to-distal movement of the guide pin 50 relative to the assembled collection cannula 12 and cutting device 30. In this regard, the guide pin 50 cannot pass completely through the assembly of the collection cannula 12 and the cutting device 30.

The bone harvesting tool 10 further includes a cap 60 having a generally semi-spherical knurled outer surface. An externally threaded nipple 62 extends from the planar base of the cap 60 and is configured for threaded engagement in the internally threaded open proximal end 14 of the collection cannula 12. A passage 64 extends centrally through the cap 60 including the nipple 62. Thus, the passage 64 can communicate with the lumen 18 in the collection cannula 12.

The bone harvesting tool 10 is assembled by threadedly engaging the cutting device 30 to the distal end 16 of the collection cannula 12. The guide pin 50 then is inserted distally through the collection cannula 12 and partly through the cutting device 30. In this fully mounted condition, the pointed distal end 54 of the guide pin 50 projects distally beyond the cutting device 30. The cap 60 then is threadedly engage with the proximal end 14 of the collection cannula 12 so that the knurled portion 56 adjacent the proximal end 52 of the guide pin 50 projects into the passage 64 in the cap 60, but does not project proximally beyond the cap 60.

The assembled bone harvesting tool 10 is used by positioning the pointed distal end 54 of the guide pin 50 at the targeted site for bone harvesting and aligning the bone harvesting tool 10 at an appropriate approach angle. The surgeon then applies distally directed pressure to the cap 60 and rotates the bone harvesting tool 60 by employing the handle 24. As a result, the blades 38 of the cutting device 30 advance into the targeted region of the bone tissue. The angular alignment of the blades 38 causes the cut bone tissue to advance axially through the center of the cutting device 30 and into the lumen 18 of the collection cannula 12. Movement of the bone tissue into the collection cannula 12 causes the guide pin 50 to move axially through the lumen 18 in a proximal direction so that the proximal end 52 of the guide pin 50 advances farther from the semi-spherical surface of the cap 60. The surgeon can monitor the collection process by observing the proximal advance of the guide pin 50 and by observing the harvested bone tissue through the openings 20 in the collection cannula 12. The numeric indicia 22 on the exterior of the collection cannula are employed to monitor both the advance of the bone harvesting tool 10 into the patient and to accurately determine the amount of harvested bone tissue in the lumen 18 of the collection cannula 12.

The rotation of the tool 10 is stopped when the surgeon determines that a sufficient volume of bone tissue has been collected and/or when the surgeon determines that the cutting device 30 has advanced sufficiently into the targeted area of the bone. If necessary, the surgeon can access a different location if additional bone tissue is required. Furthermore, the surgeon can adjust the angle of the longitudinal axis of the collection cannula 12 to collect additional bone tissue in a slightly different region of the targeted site.

The bone harvesting device 10 is removed from the patient when a sufficient volume of bone tissue has been harvested. The surgeon then removes the cutting device 30 by inserting a pin (not shown) into the aperture 44 and unthreaded the cutting device 30. The collected bone tissue in the lumen 18 of the collection cannula 12 then is expelled merely by exerting a distal force on the proximal end 52 of the guide pin 50. This force urges the guide pin 50 in a distal direction, and the plug 58 of the guide pin 50 urges the collected bone tissue from the distal end 16 of the collection cannula 12.

The invention has been described with respect to a preferred embodiment. However, it is apparent that various changes can be made without departing from the scope of the invention. For example, the invention may be directed to a system of bone harvesting tools. Various components of the system may be interchangeable with one another. For example, the system may include collection cannula with different lengths or cross-sectional dimension depending upon size or other characteristics of the patient and the amount of bone tissue that must be harvested. This system may include a plurality of cutting devices 30 with different sizes or configurations. All of the cutting devices 30 preferably are mountable on any of the collection cannula of the system.

The cap shown in the preferred embodiment has a generally semi-spherical outer surface. However, caps with other configurations can be provided, and in certain instances the cap may be unnecessary.

The preferred embodiment illustrates a transverse handle for gripping the tool 10 and for applying rotational force. However, handles of other configurations can be utilized. For example, a generally disc-shaped handle with finger grips on the outer circumference can be employed in place of the handle 24 shown above. Furthermore, proximal portions of the collection cannula 12 can be configured for mating with a rotatable tool.

What is claimed is:

1. A bone harvesting tool comprising:
   an elongated collection cannula having a proximal end, a distal end and a lumen extending between the ends, the lumen having a selected inside diameter from the proximal end toward the distal end;
   a cutting device having a proximal end removably mounted to the distal end of the collection cannula, a distal end configured for cutting bone tissue from a patient and a passage extending between the ends for permitting the cut bone tissue to advance proximally into the lumen of the collection cannula, the collection cannula and the cutting device having a combined length from the proximal end of the collection cannula to the distal end of the cutting device;
   a handle mounted to the collection cannula at a position near the proximal end of the collection cannula, the handle projecting transversely of the collection cannula to enable application of rotational force to the cutting device;
   a cap removably mounted threadedly substantially at the proximal end of the collection cannula, the cap having a convex semi-spherical proximal surface, and an opening having a non-threaded inner surface extending through the convex semi-spherical surface and communicating with the lumen of the collection cannula; and
   a non-threaded guide pin telescoped into the lumen of the collection cannula, the guide pin having a pointed distal end cross-sectionally dimensioned to project through the passage of the cutting device, a proximal end and a length exceeding the combined length of the collection cannula and the cutting device, the guide pin further having a diameter smaller than the selected inside diameter of the lumen of the collection cannula and smaller than the opening extending through the convex semi-spherical proximal surface of the cap, at least the proximal end of the guide pin being configured for reception in the opening in the cap, the guide pin further including a plug in proximity to the distal end of the guide pin, the plug having an outside diameter slightly smaller than the inside diameter of the lumen, the plug being slideable in proximal and distal directions within the collection cannula and being sufficiently large for urging collected bone tissue from the collection cannula in response to distally directed forces exerted on the proximal end of the guide pin.

2. The bone harvesting tool of claim 1, wherein the plug is dimensioned relative to the distal end of the collection cannula to limit axial advancement of the guide pin into the cutting device.

3. The bone harvesting tool of claim 1, wherein the cutting device includes a plurality of blades converging towards one another at further positions from the collection cannula.

4. The bone harvesting tool of claim 3, wherein the cutting device includes, a mounting ring at the proximal end of the cutting device, the mounting ring being threadedly engageable with the distal end of the collection cannula.

5. The bone harvesting tool of claim 1, wherein regions of the guide pin adjacent the proximal end thereof include a pattern of knurling to facilitate digital manipulation of the guide pin.

6. The bone harvesting tool of claim 1, wherein the collection cannula is formed with a single linear array of transverse holes spaced equally apart along the longitudinal direction of the collection cannula for permitting visual observation of bone tissue collected in the lumen of the collection cannula, the transverse holes being sufficiently narrow to prevent collected bone tissue from exiting the collection cannula through the transverse holes, the collection cannula being marked with numeric indicia of measurement in proximity to the respective transverse holes.

* * * * *